(12) United States Patent
Chou

(10) Patent No.: US 6,473,909 B1
(45) Date of Patent: Nov. 5, 2002

(54) FRAME FOR SWIMMING/DIVING GOGGLES

(76) Inventor: Terry Chou, No. 12, Hsin Ho Herng Rd., Tainan City (TW)

( * ) Notice: Subject to any disclaimer, the term of this patent is extended or adjusted under 35 U.S.C. 154(b) by 0 days.

(21) Appl. No.: 09/920,183

(22) Filed: Aug. 2, 2001

(51) Int. Cl.[7] .................................................. A61F 9/02
(52) U.S. Cl. ........................................................ 2/428
(58) Field of Search .......................... 2/428, 429, 430, 2/9, 439, 440, 426

(56) References Cited

U.S. PATENT DOCUMENTS

| | | | |
|---|---|---|---|
| 3,694,814 A | * 10/1972 | DeBarbieri et al. ............ | 2/428 |
| 4,087,865 A | * 5/1978 | Garofalo .......................... | 2/428 |
| 6,098,206 A | * 8/2000 | Chou .............................. | 2/428 |
| 6,317,897 B1 | * 11/2001 | Chiang ........................... | 2/428 |

* cited by examiner

*Primary Examiner*—Peter Nerbun
(74) *Attorney, Agent, or Firm*—Charles E. Baxley

(57) ABSTRACT

A frame for swimming/diving goggles comprises an inner rigid frame and a covering that is made of a soft, tensile material and that covers at least a portion of the inner rigid frame. The frame comprises two lens-engaging portions and a bridge connecting the lens-engaging portions, the lens-engaging portions and the bridge being formed by the inner rigid frame and the covering. In another embodiment of the invention, the frame comprises a lens-engaging portion defined by the inner rigid frame and the covering.

2 Claims, 8 Drawing Sheets

FRAME FOR SWIMMING/DIVING GOGGLES

BACKGROUND OF THE INVENTION

1. Field of the Invention

The present invention relates to a frame for swimming/diving goggles that provides improved wearing comfort, improved safety, and appearance diversity without sacrificing the strength.

2. Description of the Related Art

FIGS. 5 and 6 of the drawings illustrate a pair of conventional swimming goggles comprising two lenses 1', a frame 2', a two padding members 3', and a head strap 4'. Each lens 1 is made of a rigid material and includes a flange (not shown) for engaging with an associated padding member 3'. The frame 2' is made of a soft material and includes two frame portions connected by a bridge 21', each frame portion having a receiving hole 22' for receiving an associated lens 1'. Each receiving hole 22' includes two protrusions 23' for engaging with two engaging slot 11' (only one is shown) in the associated lens 1'. Each frame portion further includes an engaging portion 24' on an outer end thereof for engaging with the head strap 4'. A central axis A (FIG. 6) of one of the lenses 1' and the associated frame portion is kept coincident with that of the other lens 1' and its associated frame portion by means of rigidity of the frame 2. However, the rigidity of the frame 2' causes an uncomfortable wearing. In addition, the rigid frame 2', if impinged during swimming, might break and thus cause injury.

FIGS. 7 and 8 illustrate another pair of conventional swimming goggles comprising two lenses 5', a frame 6', two padding members 7', and a head strap 8'. Each lens 5' is made of a rigid material and includes a flange 51' for engaging with the frame 6' and an associated padding member 7'. The frame 6' is made of a soft, tensile material and includes two frame portions connected by a bridge 61'. Each frame portion includes a receiving hole 62' for receiving an associated lens 5' and an engaging portion 63' for engaging with the head strap 8'. The soft, tensile frame 6' allows easy engagement of the flange 51' into the associated receiving hole 62' and provides improved wearing comfort. However, since the frame 6' is soft, a central axis B of the one of the lenses 5' and the associated frame portion cannot be kept coincident with that of the other lens 5' and its associated frame portion after assembly, as shown in FIG. 6. Namely, the lens 5' tends to be disengaged from the soft, tensile frame 6' as a result of insufficient holding force provided by the frame 6' or fatigue of the frame 6'.

SUMMARY OF THE INVENTION

An object of the present invention is to provide a frame for swimming/diving goggles that provides improved wearing comfort, improved safety, and appearance diversity without sacrificing the strength.

In accordance with the present invention, a frame for a pair of swimming/diving goggles comprises an inner rigid frame and a covering that is made of a soft, tensile material and that covers at least a portion of the inner rigid frame. The frame comprises two lens-engaging portions and a bridge connecting the lens-engaging portions, the lens-engaging portions and the bridge being formed by the inner rigid frame and the covering. At least one lateral extension extends from the inner rigid frame, wherein at least a portion of the lateral extension is exposed in an area covered by the covering. The inner rigid frame has at least one disconnected section that is filled with the covering. The soft, tensile covering allows easy engagement with the lens and the lens is securely in the frame by the inner rigid frame. The soft, tensile covering provides improved wearing comfort and safety. In another embodiment of the invention, the frame comprises a lens-engaging portion defined by the inner rigid frame and the covering.

Other objects, advantages, and novel features of the invention will become more apparent from the following detailed description when taken in conjunction with the accompanying drawings.

DETAILED DESCRIPTION OF THE PREFERRED EMBODIMENTS

Figure 1:
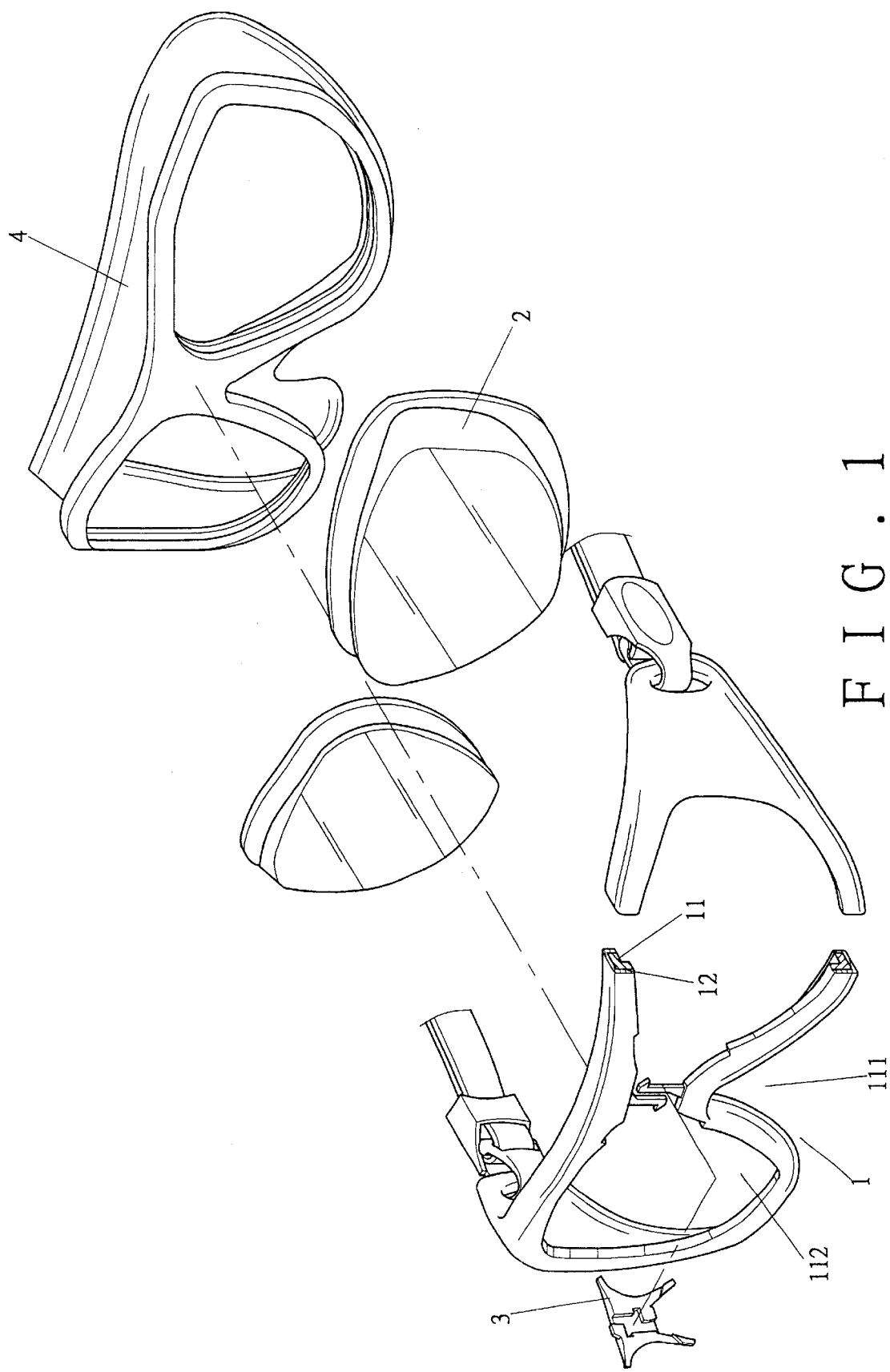
FIG. 1 is an exploded perspective view of a pair of swimming/diving goggles with a frame in accordance with the present invention.
Figure 2:
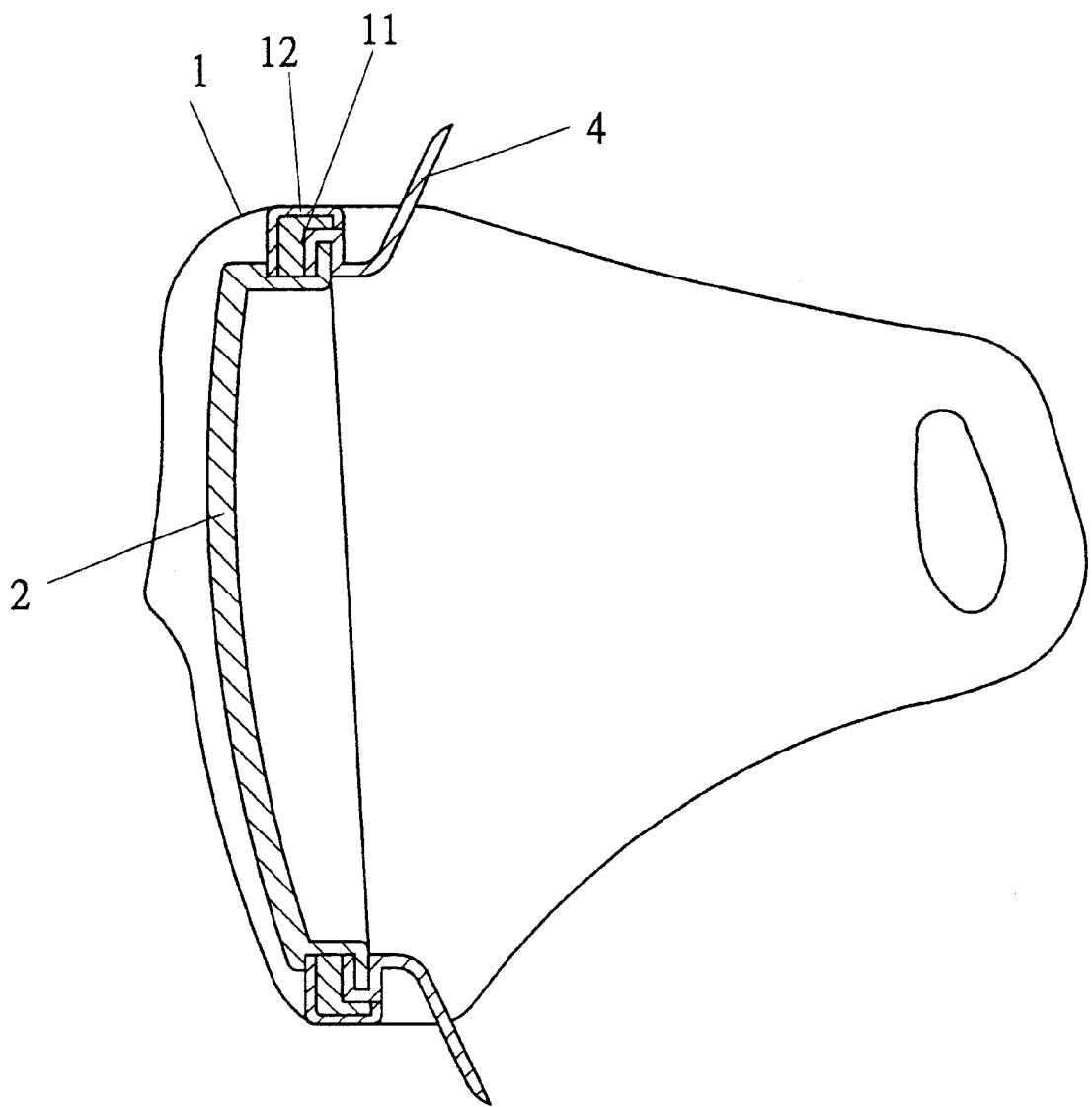
FIG. 2 is a sectional view of the pair of swimming/diving goggles in FIG. 1.

Referring to FIGS. 1 through 4 and initially to FIGS. 1 and 2, a pair of swimming/diving goggles in accordance with the present invention generally includes two lenses 2, a frame 1, and a padding member 4. The frame 1 in accordance with the present invention comprises a rigid inner frame 11 and an outer soft covering 12. The inner frame 11 comprises a bridge 111 in a middle thereof and two lens-engaging portion 112. The outer soft covering 12 is a layer of soft, tensile material covering at least a portion of an outer periphery of the inner frame 11. The frame 1 is formed by means of placing the inner rigid frame 11 in a mold and then pouring liquid material into the mold. After hardening, a soft, tensile covering 12 is formed on the inner rigid frame 11.

In assembly, each lens 2 is engaged with the padding member 4 and then engaged in the associated lens-engaging portion 112. Next, a connecting block 3 is engaged with a corresponding portion of the frame 1 to thereby securely retain the lenses 2 in the lens-engaging portions 112, respectively. Since the frame 1 includes the inner rigid frame 11, a central axis of one of the lenses 2 and its associated lens-engaging portion 112 is kept coincident with that of the other lens 2 and its associated lens-engaging portion 112. In addition, the soft covering 12 provides improved wearing comfort to the frame 1 while reducing the possibility of breakage when the frame 1 is impacted. Thus, the safety of the frame 1 is improved.

Figure 3:
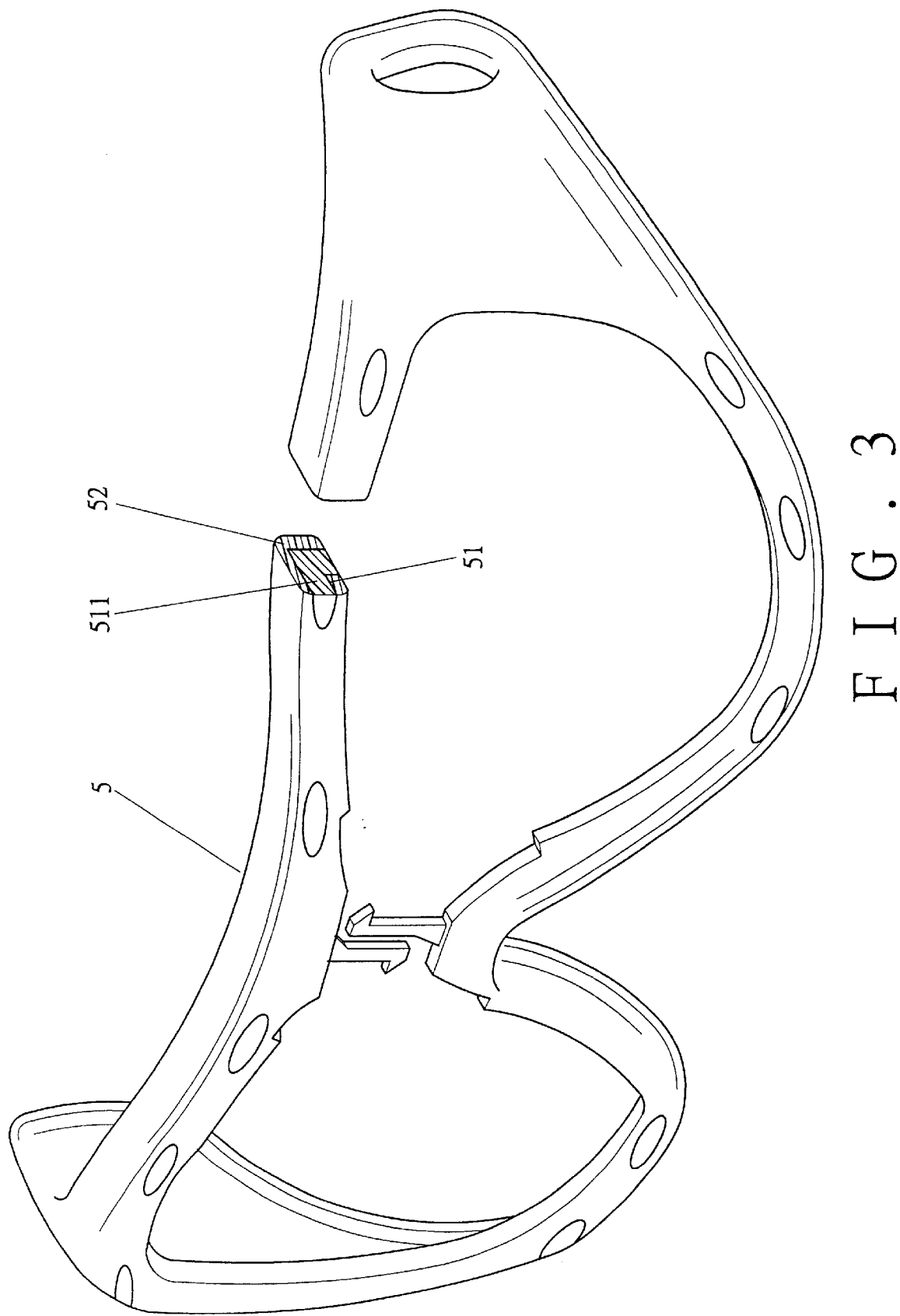
FIG. 3 is a perspective view, partly cutaway, of a pair of swimming/diving goggles with another embodiment of the frame in accordance with the present invention.

FIG. 3 illustrates a modified embodiment of the frame (now designated by 5) in accordance with the present invention. In this embodiment, the frame 5 comprises an inner rigid frame 51 having at least one lateral extension 511. The lateral extension 511 is partially exposed in an area covered by the soft, tensile covering 52. Thus, a frame with appearance diversity is provided.

Figure 4:
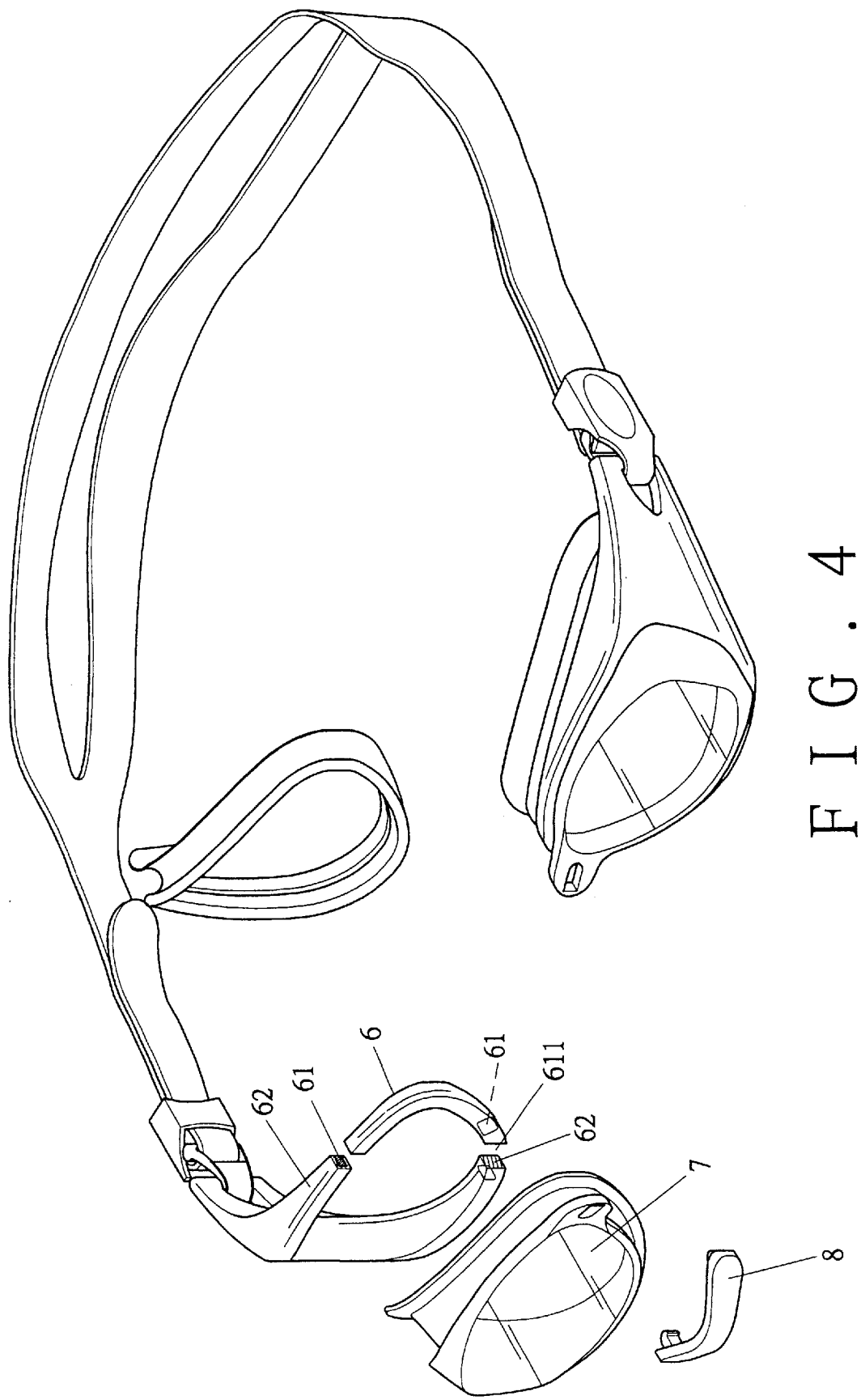
FIG. 4 is a perspective view, partly exploded, of a pair of swimming/diving goggles with a further embodiment of the frame in accordance with the present invention.
Figure 5:
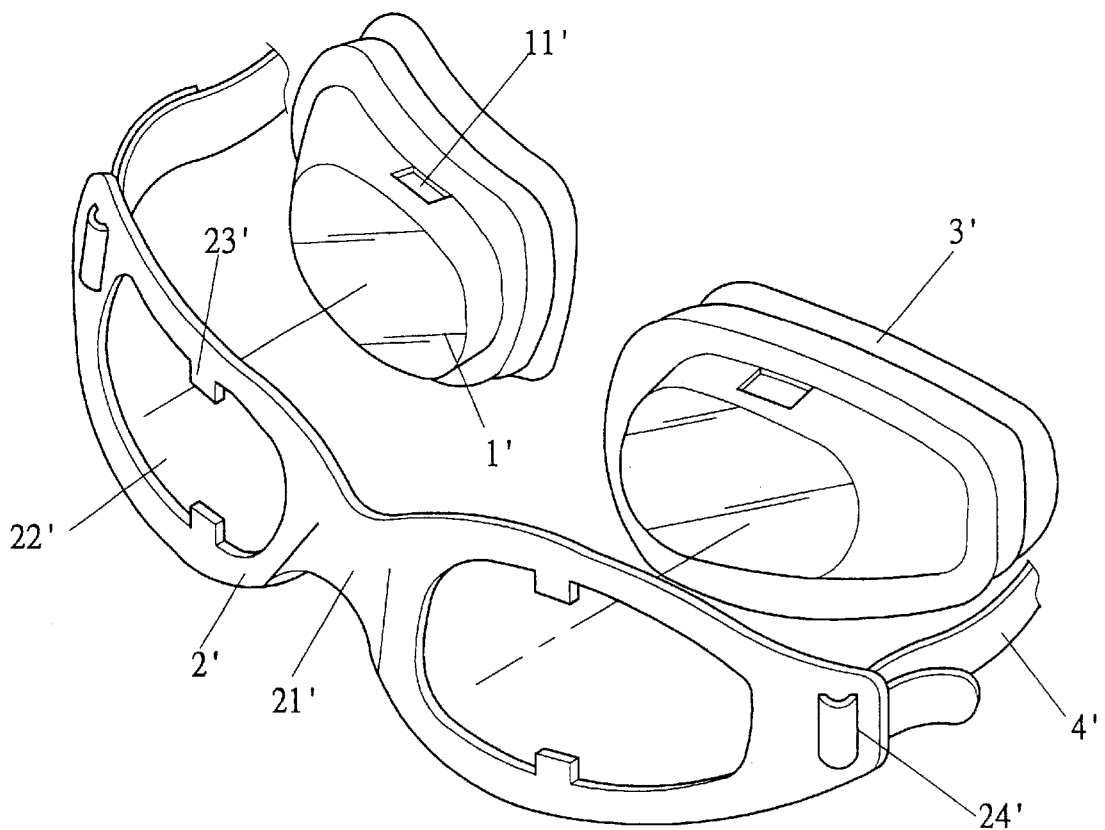
FIG. 5 is an exploded perspective view of a pair of conventional swimming goggles.
Figure 6:
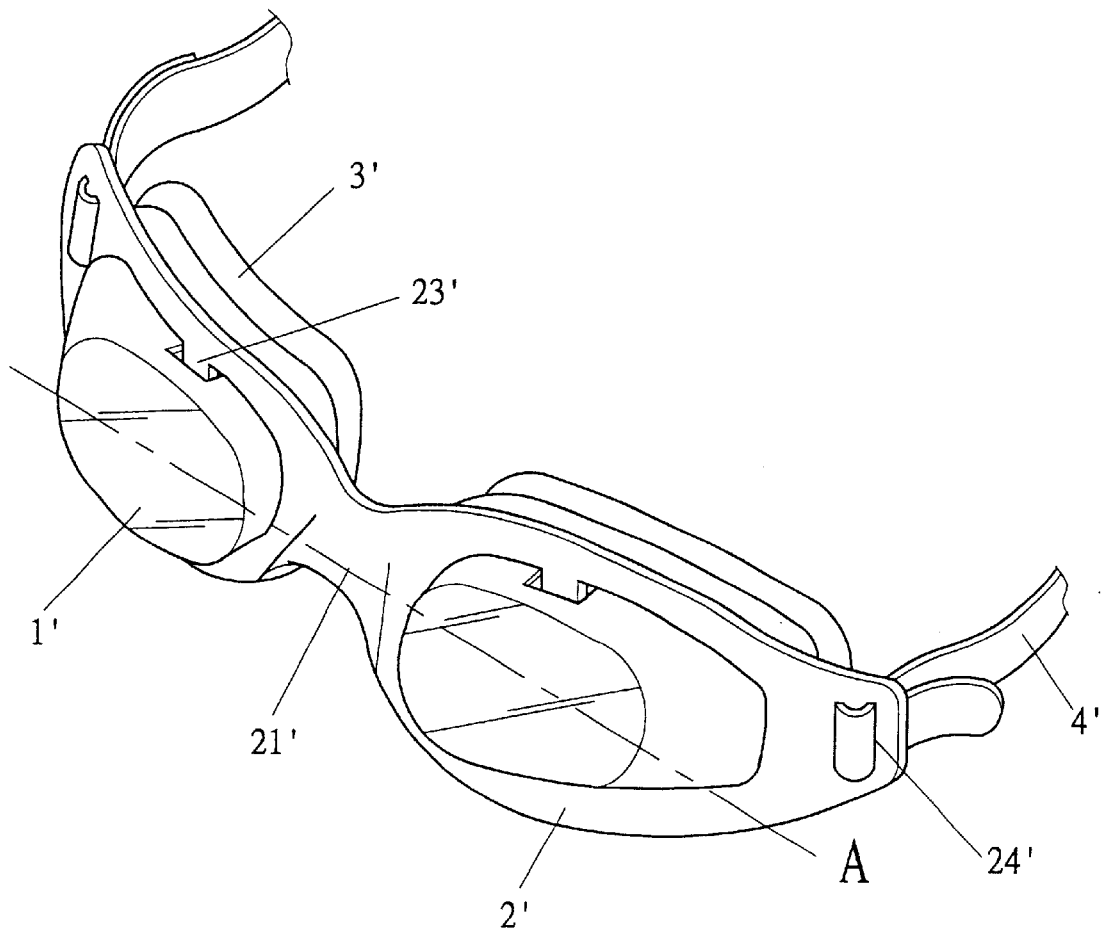
FIG. 6 is a perspective view of the pair of conventional swimming goggles in FIG. 5.
Figure 7:
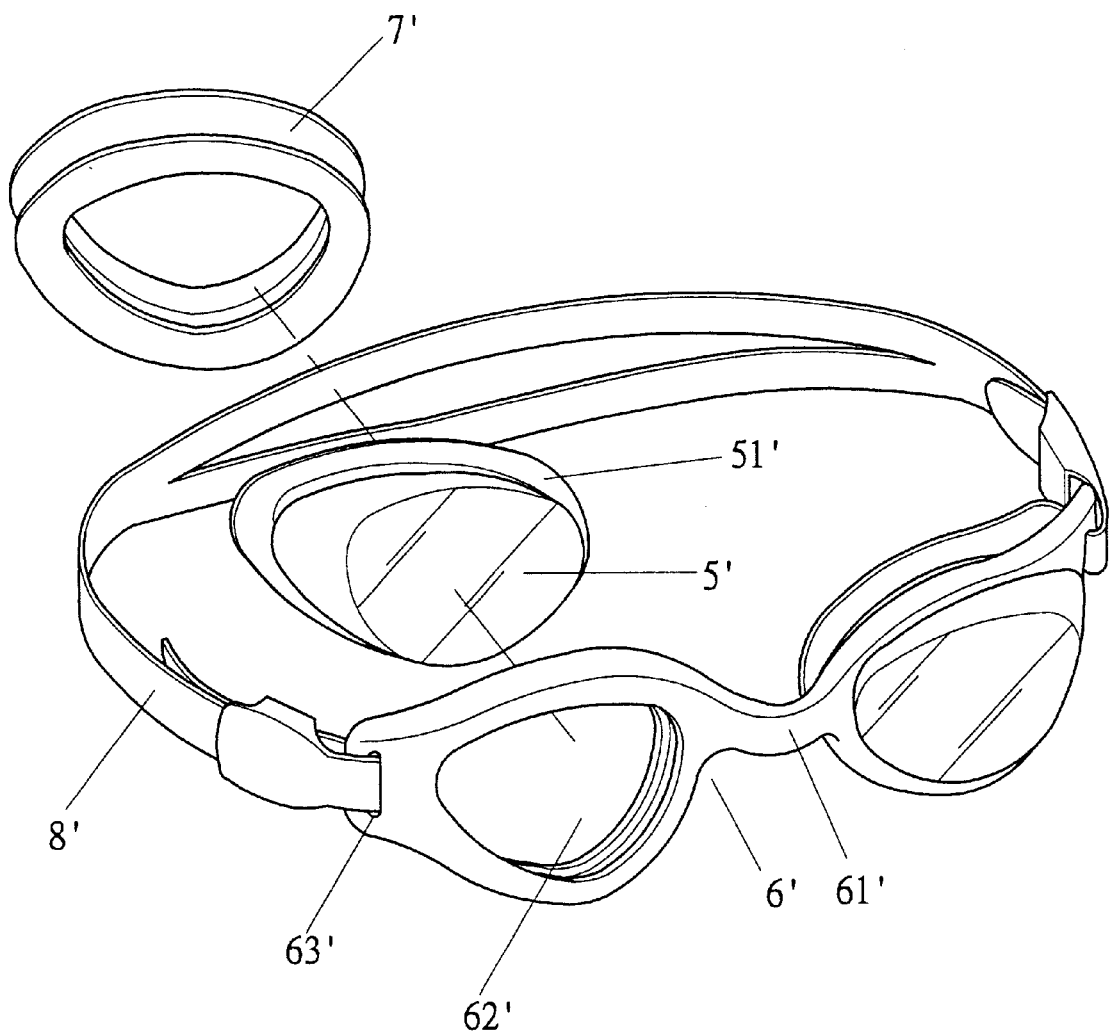
FIG. 7 is a perspective view, partly exploded, of another pair of conventional swimming goggles.
Figure 8:
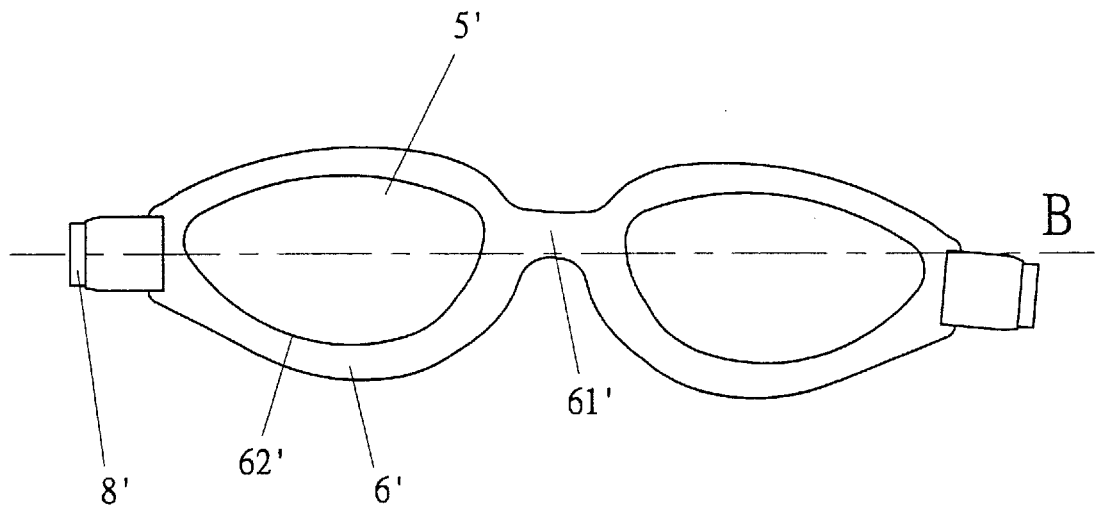
FIG. 8 is a front view of the pair of conventional swimming goggles in FIG. 7.

FIG. 4 illustrates another modified embodiment of the frame for a pair of swimming/diving goggles of the type having two separate frames 6 and two separate lens 7. A bridge 8 is connected between the frames 6. Each frame 6 comprises an inner rigid frame 61 having at least one disconnected section 611. Nevertheless, the soft, tensile covering 62 covering the inner rigid frame 61 also fills the disconnected section 611 during molding. Thus, two disconnected ends of the disconnected section 611 of the inner rigid frame 61 are connected by the covering 62 that is filled in the disconnected section 611. The soft, tensile covering 62 allows easy engagement with the lens 7 and the lens 7 is securely in the associated frame 6 by the inner rigid frame 61. The soft, tensile covering 62 provides improved wearing comfort and safety.

Although the invention has been explained in relation to its preferred embodiment, it is to be understood that many other possible modifications and variations can be made without departing from the scope of the invention as hereinafter claimed.

What is claimed is:

1. A frame for a pair of swimming/diving goggles, the frame comprising an inner rigid frame and a covering that is made of a soft tensile material that covers at least a portion of the inner rigid frame, the frame comprising two lens-engaging portions and a bridge connecting the lens-engaging portions, the lens-engaging portions and the bridge being formed by the inner rigid frame and the covering, at least one lateral extension extending from the inner rigid frame, at least a portion of said at least one lateral extension being exposed in an area covered by the covering.

2. The frame for a pair swimming/diving goggles as claimed in claim 1, wherein the inner rigid frame has at least one disconnected section that is filled with the covering.

\* \* \* \* \*